US006288258B1

(12) United States Patent
Aramata et al.

(10) Patent No.: US 6,288,258 B1
(45) Date of Patent: Sep. 11, 2001

(54) PREPARATION OF ORGANOHALOSILANES

(75) Inventors: Mikio Aramata, Annaka; Tatsuya Fujimoto, Kashima-gun; Ryuichi Saito, Kashima-gun; Masahiro Yuyama, Kashima-gun; Tetsuya Inukai; Hajime Ishizaka, both of Annaka, all of (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/694,370

(22) Filed: Oct. 24, 2000

(30) Foreign Application Priority Data

Oct. 25, 1999 (JP) .................................................. 11-303106

(51) Int. Cl.$^7$ ....................................................... C07F 2/16
(52) U.S. Cl. ............................................................ 556/472
(58) Field of Search ............................................... 556/472

(56) References Cited

U.S. PATENT DOCUMENTS

| 4,602,101 | 7/1986 | Halm et al. . | |
| 5,973,177 | * 10/1999 | Kuivila et al. | 556/472 |
| 6,057,469 | 5/2000 | Margaria et al. . | |
| 6,090,966 | * 7/2000 | Nakanishi et al. | 556/472 |
| 6,175,030 | * 1/2001 | Kalchauer et al. | 556/472 |

FOREIGN PATENT DOCUMENTS 237892    11/1969  (RU) .

OTHER PUBLICATIONS

Komitsky, Frank, Jr., et al., "The Influence of Promoter Levels on the Direct Synthesis," *Silicon for the Chemical Industry IV*, Geiranger, Norway, pp. 217–225 (1998).

* cited by examiner

*Primary Examiner*—Paul F. Shaver
(74) *Attorney, Agent, or Firm*—Millen, White, Zelano & Branigan, P.C.

(57) ABSTRACT

When oganohalosilanes are prepared by charging a reactor with a contact mass containing metallic silicon and a copper catalyst and introducing an organohalide-containing gas into the reactor to effect the direct reaction, 50–10,000 ppm of bronze phosphide is added to the contact mass. The invention is successful in efficiently producing organohalosilanes in a high STY and low T/D.

20 Claims, 2 Drawing Sheets

PREPARATION OF ORGANOHALOSILANES

This invention relates to a process for preparing organohalosilanes, and more particularly, to a direct synthesis process for continuously preparing organohalosilanes by effecting gas-solid catalytic reaction between metallic silicon and organohalide in the presence of a copper catalyst.

BACKGROUND OF THE INVENTION

With respect to the synthesis of organohalosilanes, Rochow first disclosed in U.S. Pat. No. 2,380,995 direct synthesis reaction between metallic silicon and organohalide in the presence of a copper catalyst. Since then, there have been reported a number of research works relating to copper catalysts and treatment thereof, co-catalysts used together with copper catalysts, reactors, additives used during reaction, and the like. In the industrial synthesis of organohalosilanes, the selectivity of diorganodihalosilane which is most widely used in silicone resins, the formation rate of silanes, and the percent conversion of metallic silicon into useful silane are crucial. The selectivity of diorganodihalosilane is evaluated in terms of a weight or molar ratio of dialkyldihalosilane to the silanes produced and a T/D ratio. Organohalosilane products contain diorganodihalosilane (D), triorganohalosilane (M), organotrihalosilane (T), etc. as well as other by-products such as organohydrodihalosilane (H) and organohalodisilanes. Particularly when silicones are manufactured using the direct method organohalosilane product as a starting material, few processes are available for the effective utilization of disilanes known as a high-boiling fraction. Thus, most disilanes are discarded as the residue.

The T/D ratio is a compositional ratio of organotrihalosilane to diorganodihalosilane in the entire organohalosilanes produced, with a lower T/D ratio being preferred. The formation rate of organohalosilane is represented by a space time yield (STY) which is the weight of crude organohalosilane produced per unit time relative to the weight of metallic silicon held in the reactor. In order to improve the content of diorganodihalosilane produced, reduce the T/D ratio or increase the STY, various research works have been made with a focus on the catalyst and promoter.

U.S.S.R. Application Specification No. 1,152,943 (Certificate of inventorship No. 237,892) dated Nov. 20, 1969 discloses to add a phosphorus-copper-silicon alloy to a contact mass so as to give 2,500 to 30,000 ppm of phosphorus, thereby improving the dimethyldichlorosilane content to 82.3%. Use of a promoter-containing metallic silicon alloy is not adequate to industrial scale reaction, and the STY and silane composition are unsatisfactory. U.S. Pat. No. 4,602,101 corresponding to JP-B 5-51596 discloses that 25 to 2,500 ppm of a phosphorus compound capable of generating elemental phosphorus in the reactor is added to a contact mass. Although the results of reaction according to this U.S. patent are improved over the U.S.S.R. patent, there still remain many problems including hazard imposed by spontaneously igniting elemental phosphorus and increased cost of raw materials. Then this U.S. patent is also unsuitable to apply to commercial scale reactors. There is no teaching about the effect available with a phosphorus concentration of at least 2,500 ppm. Also, F. Komitsky et al., Silicon For the Chemical Industry IV, Geiranger, Norway (1998), page 217, proposes the addition of phosphorus in the form of copper phosphide, leaving problems including a low percent conversion, ineffective utilization of phosphorus, and difficult control of a phosphorus concentration.

JP-A 11-228580 or EP 893408 (Pecine Electrometallurgy) discloses that active silicon powder is prepared by milling metallic silicon in a rod mill or ball mill using rods or balls of bronze phosphide whereby bronze phosphide finely adheres to surfaces of silicon particles, rendering the silicon particles active. The bronze phosphide used therein is ordinary bronze phosphide having a phosphorus concentration of up to 1% by weight. Phosphorus is added in the form of iron phosphide. This gives rise to essentially the same problem as the prior art proposals.

SUMMARY OF THE INVENTION

An object of the invention is to provide a direct synthesis process for preparing organohalosilanes in a low T/D ratio and a desired STY while restraining the formation of disilanes.

It is desirable to have a process for preparing organohalosilanes by the industrially advantageous direct method, and especially a direct synthesis process for preparing organohalosilanes in the desired STY while increasing the content of diorganodihalosilane and restraining the formation of unnecessary disilanes. We have found that when a specific amount of bronze phosphide is added to the reaction contact mass containing metallic silicon, phosphorus and tin in the bronze phosphide cooperate so as to restrain the formation of disilanes while maintaining reaction activity, whereby the content of diorganodihalosilane is enhanced.

The invention provides a process for preparing oganohalosilanes comprising the steps of charging a reactor with a contact mass containing metallic silicon and a copper catalyst, and introducing an organohalide-containing gas into the reactor to effect reaction to form organohalosilanes of the following general formula (1):

$$R_nH_mSiX_{(4-n-m)} \qquad (1)$$

wherein R is a monovalent hydrocarbon group, X is a halogen atom, n and m each are an integer of 0 to 4, wherein 50 to 10,000 ppm of bronze phosphide is added to the contact mass.

DESCRIPTION OF THE PREFERRED EMBODIMENTS

Figure 1:
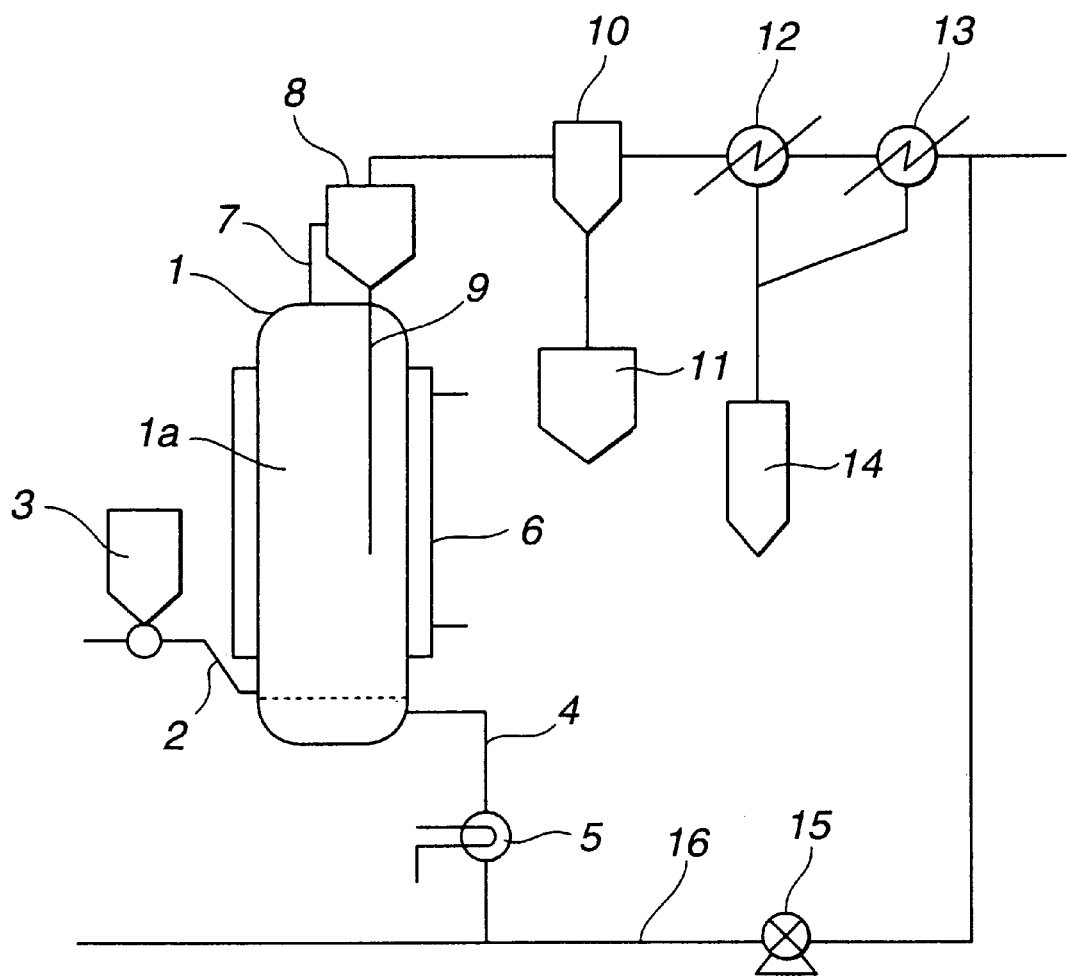
FIG. 1 schematically illustrates a system for the preparation of organohalosilanes.
Figure 2A:
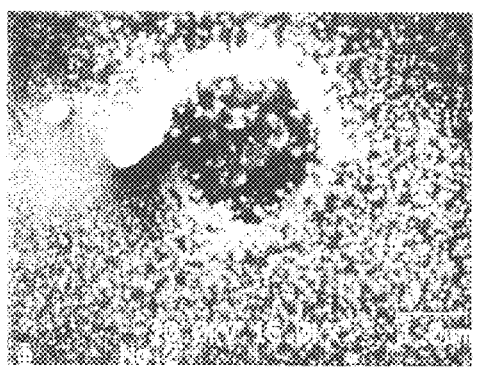
FIG. 2 illustrates the results of analysis by x-ray microanalyzer on the silicon wafer surface after a silicon wafer having bronze phosphide rested thereon is heated, FIGS. 2A, 2B, 2C and 2D being SEM images of SEI, Cu map, Sn map, and P map, respectively.
Figure 2C:
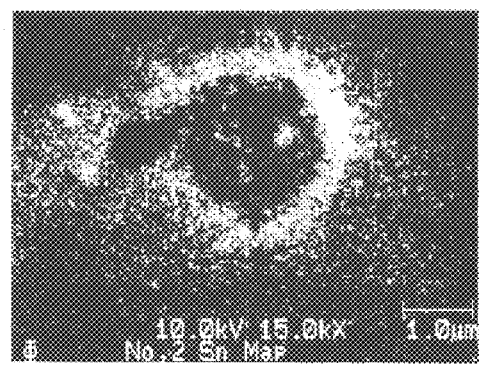
Figure 2B:
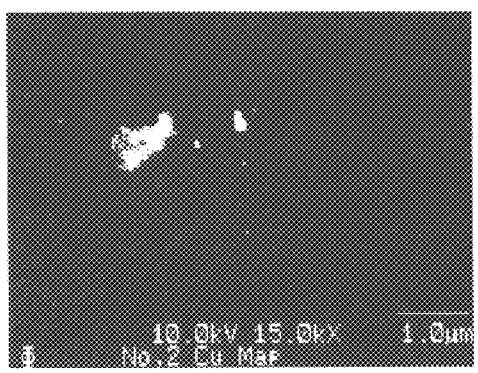
Figure 2D:
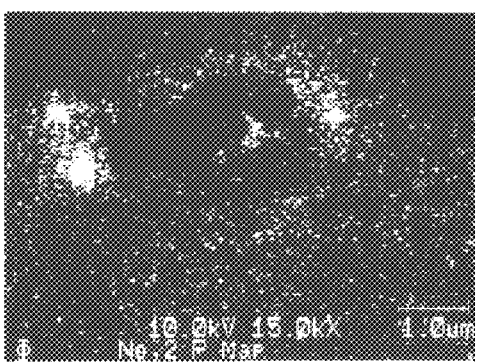

The process for preparing oganohalosilanes according to the invention involves the steps of charging a reactor with a contact mass containing metallic silicon and a copper catalyst and introducing an organohalide-containing gas into the reactor to effect the direct reaction.

The metallic silicon used herein preferably has a silicon purity of at least 97% by weight, especially at least 98% by weight. Prior to use, the metallic silicon is preferably ground into particles with an appropriate particle size. Where the reactor used is a fluidized bed or stirred bed reactor, the metallic silicon powder should preferably have a particle size in the range of 10 to 100 μm, corresponding to 50% of the mass base cumulative size distribution curve.

The copper catalyst used herein may be selected from various forms of copper including powdered copper, cuprous oxide, cupric oxide, copper halides and other copper compounds.

Any of promoters such as zinc, tin, antimony and arsenic may be used as the co-catalyst. The co-catalyst may be used as a single metal powder or compound or an alloy or compound with copper. Examples of the co-catalyst which can be commonly used include metallic zinc, metallic tin, metallic antimony, metallic arsenic powder, and halides and oxides of these metals, optionally in admixture with halides and oxides of copper, as well as copper alloys such as Cu—Zn, Cu—Sn, and Cu—Zn—Sn (or Sb or As). The copper catalysts may be admitted into the reactor alone or as an alloy along with metallic silicon.

An appropriate amount of the copper catalyst blended is about 0.1 to 30 parts, and more preferably about 2 to 8 parts by weight per 100 parts by weight of the metallic silicon. Where the co-catalyst is used, zinc is used in an amount of 0.05 to 1.0 part by weight per 100 parts by weight of the metallic silicon, and tin is used in an amount of 0.001 to 0.1 part by weight per 100 parts by weight of the metallic silicon. Antimony and arsenic are used in a single or total amount of 0.001 to 0.05 part, especially 0.05 to 0.01 part by weight per 100 parts by weight of the metallic silicon.

According to the invention, bronze phosphide is added to the contact mass. The bronze phosphide used herein preferably has a tin concentration of 1 to 30% by weight and a phosphorus concentration of 1 to 15% by weight, based on the weight of copper. More preferably the bronze phosphide has a tin concentration of 5 to 15% by weight and a phosphorus concentration of 10 to 15% by weight, especially 10 to 13% by weight, based on the weight of copper. The bronze phosphide used herein is characterized by a high phosphorus concentration of 1 to 15% by weight, in contrast with ordinary bronze phosphide having a phosphorus concentration of less than 1% by weight.

The bronze phosphide used herein preferably has a mean particle size of 1 to 200 μm, more preferably 5 to 200 μm, further preferably 5 to 50 μm, and most preferably 5 to 30 μm. Particles with a too small mean particle size may scatter away from the reaction system during fluidization, failing to exert the effect. Particles with a too large mean particle size may accumulate at the bottom of the contact mass and not fully disperse throughout the contact mass.

Products commercially available from Rare Metallic Company, for example, are useful as the bronze phosphide.

An appropriate amount of bronze phosphide blended is 50 to 10,000 parts by weight per million parts by weight of the contact mass (consisting essentially of metallic silicon and catalyst), and preferably 100 to 5,000 ppm. A less amount of bronze phosphide is insufficient to exert its effect whereas an excessive amount may cause agglomeration.

The organohalide to be reacted with metallic silicon to form organohalosilanes is typically represented by the general formula (2).

$$RX \tag{2}$$

Herein, R is a monovalent hydrocarbon group, preferably of 1 to 12 carbon atoms, for example, alkyl groups such as methyl, ethyl, propyl, butyl and hexyl, alkenyl groups such as vinyl, allyl, propenyl and butenyl, aryl groups such as phenyl and tolyl, and aralkyl groups such as benzyl, phenylethyl and phenylpropyl. X is a halogen atom such as chlorine or bromine. Illustrative examples of the organohalide include methyl chloride, ethyl chloride, methyl bromide, ethyl bromide, and benzene chloride. Of these, methyl chloride and benzene chloride are useful in the industry, with methyl chloride being most useful.

The organohalide is previously heated and gasified before it is admitted into the reactor. The organohalide gas may be fed alone or combined with an inert gas. The amount of the organohalide gas fed together with the inert gas is a sufficient amount to fluidize the contact mass, the fluidizing amount being determined as appropriate from the diameter of the reactor and the superficial velocity.

In the step of heating the contact mass or imparting catalytic activity to the contact mass, an inert gas is used for fluidizing the contact mass in the reactor. Such an inert gas may be nitrogen or argon gas, for example, with the nitrogen gas being preferable from the economic standpoint. The flow velocity of the inert gas fed in this and subsequent steps is at least the minimum fluidization velocity of the contact mass, and preferably about 5 times the minimum fluidization velocity. A flow velocity below the range of the inert gas may often fail to achieve uniform fluidization of the contact mass. If the flow velocity of the inert gas is above the range, metallic silicon powder may be excessively scattered with increased losses of the inert gas and heat. It is recommended to recycle the inert gas.

After the contact mass is given catalytic activity as mentioned above, the organohalide is introduced into the reactor where gas-solid catalytic reaction takes place between the organohalide and silicon to form organohalosilanes. The conditions for this gas-solid reaction are as used in the conventional Rochow method, and for example, the reaction temperature is 250 to 350° C.

Any desired apparatus is used in the practice of the invention. FIG. 1 illustrates one exemplary system for preparing organohalosilanes. The system includes a fluidized bed reactor 1 and a reactant source tank 3 connected to the bottom of the reactor 1 through a reactant feed conduit 2, whereby metallic silicon and a copper catalyst or a mixture of a copper catalyst and a co-catalyst are admitted into the bottom of the reactor 1. A conduit 4 for the other reactant, organic halide has a heater 5 inserted therein and is connected to the reactor 1 at the bottom. The organic halide in gas or vapor form is also introduced into the bottom of the reactor 1, thereby forming a fluidized bed 1a of the metallic silicon and the catalyst within the reactor 1. The reactor 1 is enclosed with a cooling jacket 6.

Preferably the organic halide in gas or vapor form is introduced into the reactor 1 at a linear velocity of 2 to 10 cm/sec in the steady state. Reaction is generally carried out at a temperature of 250 to 350° C.

The organohalosilane product resulting from the reaction is channeled through a discharge conduit 7 connected to the top of the reactor 1 to a first cyclone 8 where the entrained solid particles are separated and fed back to the fluidized bed 1a through a return pipe 9. The product is then fed to a second cyclone 10 where the entrained solid particles are separated and fed to a particle reservoir 11 for storage. The product is then fed to first and second silane condensers 12 and 13 where the organohalosilanes are condensed and fed to a silane reservoir 14 for storage. Part or all of the discharge gas from which solid particles have been separated and organohalosilanes have been condensed and separated is fed back to the reactor 1 through an organic halide return conduit 16 having a recycle gas compressor 15 inserted therein. The return conduit 16 is connected to the organic halide feed conduit 4.

With the process of the invention, organohalosilanes of the general formula (1):

$$R_nH_mSiX_{(4-n-m)} \tag{1}$$

are produced. Herein R and X are as defined above, n and m each are an integer of 0 to 4, with m+n≦4. In view of the supply and demand balance, it is preferred that m is approximately zero and n is approximately 2 on the average. The process of the invention yields a product having a larger proportion of diorganohalosilane (D) wherein n=2 and m=0, usually 75 to 95%, and especially 85 to 93% of diorganohalosilane (D). On the other hand, the amount of organotrihalosilane (T) wherein n=1 and m=0 produced is small. Usually, the T/D is 10% or less, and especially 7% or less. The amount of a high-boiling fraction including disilanes is also small, and usually 6% or less, and especially 3% or less.

EXAMPLE

Examples of the invention are given below by way of illustration and not by way of limitation. All parts and percents are by weight.

Experiment

An analysis is described below for demonstrating the effect of bronze phosphide. Copper phosphide and bronze phosphide were rested on a semiconductor grade silicon wafer having a mirror finish surface ((100) face). This was heated in a methyl chloride atmosphere at 300° C. for 3 hours. After cooling, the wafer surface was examined by an x-ray microanalyzer. The results are shown in the photomicrographs of FIG. 2. The portion where bronze phosphide was present showed a certain spread on the silicon wafer, and it was observed that phosphorus and tin both having a co-catalytic capability acted in an effective manner.

FIG. 2 is a set of SEM images of X15,000 magnification. FIG. 2A is a secondary electron image (SEI), FIG. 2B is a Cu map, FIG. 2C is a Sn map, and FIG. 2D is a P map. In the SEI, a spread at and around bronze phosphide is observed, and the Sn and P images indicate the presence of Sn and P in that spread.

fraction method, a specific surface area of 0.80 m$^2$/g as measured by the air-permeability method, and a bulk specific gravity of 1.9 g/cm$^3$ and a co-catalyst of zinc powder. The bronze phosphide was added to the contact mass at three levels in the range of 0.01 to 0.05 %. While the reaction temperature was controlled in the range of 280 to 300° C., methyl chloride was slowly introduced into the reactor for reaction. The methyl chloride feed was ultimately increased to a linear velocity of 7 cm/sec, at which reaction was continued. During the reaction, metallic silicon powder and the copper catalyst were always replenished in amounts corresponding to losses by silane formation and losses out of the reaction system. After 72 hours, the reaction was stopped. The average rate of silane production, the percent consumption of metallic silicon, and the composition of the formed silanes are shown in Table 1.

For comparison purposes, similar reaction was effected except that 0.005% of tin powder was added to the contact mass instead of the bronze phosphide.

Table 1 also shows the proportion of dimethyldichlorosilane $(CH_3)_2SiCl_2$ (D) and the proportion of a high-boiling fraction (R) relative to the entire amount of methylchlorosilanes produced. The high-boiling fraction included products having a boiling point of higher than 70° C. under atmospheric pressure, such as disilanes. It is noted that T/D is the weight (g) of methyltrichlorosilane divided by the weight (g) of dimethyldichlorosilane in the methylchlorosilane product, and STY representative of the formation rate of organohalosilanes is [the weight (g) of organohalosilanes]/[(weight (kg) of metallic silicon)/time (hr)].

TABLE 1

|  | E1 | E2 | E3 | CE1 | CE2 | CE3 |
|---|---|---|---|---|---|---|
| Catalyst composition (pbw) | | | | | | |
| Copper catalyst | 5.0 | 5.0 | 5.0 | 5.0 | 5.0 | 5.0 |
| Zinc powder | 0.5 | 0.5 | 0.5 | 0.5 | 0.5 | 0.5 |
| Bronze phosphide (Cu—Sn—P) | 0.0500 | 0.1000 | 0.2000 | — | — | — |
| Red phosphorus | — | — | — | 0.00030 | — | 0.00030 |
| Tin powder | — | — | — | 0.00500 | 0.00500 | — |
| Copper phosphide (Cu—P) | — | — | — | — | 0.00200 | — |
| Bronze (Cu—Sn) | — | — | — | — | — | 0.10000 |
| Sn concentration (wt %/Si) | 0.00500 | 0.01000 | 0.02000 | 0.00500 | 0.00500 | 0.01000 |
| P concentration (wt %/Si) | 0.00015 | 0.00030 | 0.00060 | 0.00030 | 0.00030 | 0.00030 |
| Results of reaction | | | | | | |
| STY (g-silane/kg-Si · hr) | 161 | 179 | 210 | 110 | 137 | 155 |
| D (wt %) | 90.8 | 89.3 | 88.5 | 86.7 | 87.0 | 86.6 |
| R (wt %) | 1.9 | 2.2 | 3.2 | 3.4 | 4.5 | 5.1 |
| T/D | 0.043 | 0.053 | 0.058 | 0.068 | 0.059 | 0.069 |

Example 1

Bronze phosphide used was bronze phosphide (Cu: 79.1%, Sn: 10.1%, and P: 10.2%) commercially available from Rare Metallic Company, which was ground to a particle size of 20 to 50 μm by stamping. A steel reactor of 8 cm diameter equipped with a spiral agitator as shown in FIG. 1 was charged with 100 parts of metallic silicon powder having a mean particle size of 50 μm. With stirring by the spiral agitator, nitrogen gas was introduced into the reactor at a linear velocity of 2 cm/sec to fluidize the silicon powder while the powder was heated to 280° C. Thereafter, 3 parts of a catalyst mixture was added to the reactor. The catalyst mixture consisted of a copper catalyst in the form of copper flakes having a mean particle size of 47 μm as measured by a particle size distribution instrument using the laser dif- According to the invention, organohalosilanes can be efficiently produced in a high STY and low T/D.

Japanese Patent Application No. 11-303106 is incorporated herein by reference.

Reasonable modifications and variations are possible from the foregoing disclosure without departing from either the spirit or scope of the present invention as defined by the claims.

What is claimed is:

1. A process for preparing oganohalosilanes comprising the steps of charging a reactor with a contact mass containing metallic silicon and a copper catalyst, and introducing an organohalide-containing gas into the reactor to effect reaction to form organohalosilanes of formula (1):

$$R_nH_mSiX_{(4-n-m)} \qquad (1)$$

wherein R is a monovalent hydrocarbon group, X is a halogen atom, n and m each are an integer of 0 to 4, wherein 50 to 10,000 ppm of bronze phosphide is added to said contact mass.

2. The process of claim 1 wherein the bronze phosphide has a mean particle size of 1 to 200 μm.

3. The process of claim 1 wherein the bronze phosphide has a tin concentration of 1 to 30% by weight and a phosphorus concentration of 1 to 15% by weight.

4. The process of claim 1 wherein the metallic silicon has a purity of at least 97% by weight.

5. The process of claim 1 wherein the metallic silicon has a purity of at least 98% by weight.

6. The process of claim 1, wherein the copper catalyst is powdered copper, cuprous oxide, cupric oxide, or a copper halide.

7. The process of claim 1, wherein the copper catalyst is 0.1 to 30 parts by weight per 100 parts per weight of the metallic silicon.

8. The process of claim 1, wherein the copper catalyst is 2 to 8 parts by weight per 100 parts per weight of the metallic silicon.

9. The process of claim 1, wherein the bronze phosphide has a tin concentration of 5 to 15% by weight and a phosphorous concentration of 10 to 15% by weight.

10. The process of claim 9, wherein the bronze phosphide has a phosphorous concentration of 10 to 13% by weight.

11. The process of claim 1, wherein the bronze phosphide has a mean particle size of 5 to 200μm.

12. The process of claim 1, wherein the bronze phosphide has a mean particle size of 5 to 50μm.

13. The process of claim 1, wherein the bronze phosphide has a mean particle size of 5 to 30μm.

14. The process of claim 1, wherein 100 to 5,000 ppm of bronze phoshide is added to said contact mass.

15. The process of claim 1, wherein the organohalide has formula (2)

$$RX \qquad (2)$$

wherein R is a monovalent hydrocarbon group having 1 to 12 carbon atoms, and X is a halogen atom.

16. The process of claim 15, wherein R is methyl, ethyl, propyl, butyl, hexyl, vinyl, allyl, propenyl, butenyl, phenyl, tolyl, phenylethyl, or phenylpropyl, and X is chlorine or bromine.

17. The process of claim 15, wherein RX is methyl chloride, ethyl chloride, methyl bromide, ethyl bromide, or benzene chloride.

18. The process of claim 15, wherein RX is methyl chloride, ethyl chloride, methyl bromide, ethyl bromide or benzene chloride.

19. The process of claim 1, wherein the organohalide is introduced into the reactor at a linear velocity of 2 to 10 cm/sec in a steady state and is carried out at a temperature of 250 to 350°.

20. The process of claim 1, wherein m is 0 and n is 2.

\* \* \* \* \*